US007625579B2

(12) United States Patent
Read et al.

(10) Patent No.: US 7,625,579 B2
(45) Date of Patent: Dec. 1, 2009

(54) ANTIMICROBIAL COATINGS

(75) Inventors: Roger Read, Kensington (AU); Naresh Kumar, Maroubra (AU); Mark Wilcox, Balmain (AU); Hua Zhu, Bexley (AU); Hnas Griesser, The Patch (AU); Ben Muir, Donvale (AU); Helmut Thissen, Wheelers Hill (AU); Tim Hughes, Ferntree Gully (AU)

(73) Assignee: Unisearch Limited, Sydney, New South Wales (AU)

( * ) Notice: Subject to any disclaimer, the term of this patent is extended or adjusted under 35 U.S.C. 154(b) by 48 days.

(21) Appl. No.: 10/257,245

(22) PCT Filed: Apr. 10, 2001

(86) PCT No.: PCT/AU01/00407

§ 371 (c)(1),
(2), (4) Date: Feb. 20, 2003

(87) PCT Pub. No.: WO01/76594

PCT Pub. Date: Oct. 18, 2001

(65) Prior Publication Data
US 2003/0224032 A1   Dec. 4, 2003

(30) Foreign Application Priority Data
Apr. 10, 2000   (AU) .................... PQ6812

(51) Int. Cl.
*A61F 2/00*   (2006.01)
*A01N 43/08*   (2006.01)

(52) U.S. Cl. .............. 424/423; 424/78.06; 424/422; 424/400; 524/500; 524/537; 524/539; 536/25.3; 523/122; 514/256

(58) Field of Classification Search ............ 424/404, 424/423, 78.06, 422, 400; 428/411.1; 536/25.3; 514/256; 524/500, 537, 539; 523/122
See application file for complete search history.

(56) References Cited

U.S. PATENT DOCUMENTS

| 2,815,309 | A | * | 12/1957 | De Ganahl et al. ........ 156/214 |
| 4,572,831 | A | * | 2/1986 | Rosen ................ 106/31.03 |
| 5,705,649 | A | * | 1/1998 | Shultz et al. ............ 548/126 |
| 6,054,504 | A | * | 4/2000 | Dalla Riva Toma ....... 523/122 |

FOREIGN PATENT DOCUMENTS

| WO | 95/30409 | | 11/1995 |
| WO | 96/01294 | | 1/1996 |
| WO | WO9601294 | * | 1/1996 |
| WO | 99/01514 | | 1/1999 |
| WO | 99/05227 | | 2/1999 |
| WO | WO9905227 | * | 2/1999 |
| WO | WO 9905227 A1 | * | 2/1999 |
| WO | 99/53915 | | 10/1999 |
| WO | 99/54323 | | 10/1999 |
| WO | WO9953915 | * | 10/1999 |
| WO | WO9954323 | * | 10/1999 |
| WO | WO 9954323 A1 | * | 10/1999 |

* cited by examiner

*Primary Examiner*—M P Woodward
*Assistant Examiner*—Dennis Heyer
(74) *Attorney, Agent, or Firm*—Nixon & Vanderhye

(57) ABSTRACT

The present invention provides a substrate having a plurality of immobilised furanone moieties associated with at least part of a surface of the substrate. The invention also relates to articles consisting of or comprising such a substrate.

16 Claims, No Drawings

ANTIMICROBIAL COATINGS

FIELD OF THE INVENTION

The present invention relates to substrates having one or more bioactive species immobilized on a surface thereof. The present invention is particularly concerned with substrates having an antibacterial or antifungal species immobilized thereon and to methods of forming such substrates.

BACKGROUND

The present invention will now be described with particular reference to biomedical applications. However, it is to be understood that the present invention has applications in any area that requires increased resistance to bacterial and fungal colonization.

The colonization by bacteria of devices used for human health care and/or improvement of quality of life poses serious problems and causes adverse reactions that are detrimental to the viability and useful service life of the device. Examples of devices that are colonized by bacteria comprise implantable biomedical devices such as urinary catheters, percutaneous access catheters, stents, as well as non-implantable devices such as contact lenses, contact lens storage cases, and the like. Once attached to a surface, bacteria are much more resistant to antibiotics and other bacteriostatic and bacteriocidal agents and can proliferate, inducing adverse reactions in the host environment.

Accordingly, much work has focused on the prevention of bacterial colonization. One solution is to coat catheters with a thin layer of silver metal, which releases silver ions that act as antibacterial agents. Another solution is the surface immobilization of quaternary amine compounds (Dziabo U.S. Pat. No. 5,515,117) which are known to be antibacterial agents.

The provision of silver coatings is not practical or economic in many applications. There is also clinical evidence that silver coatings do not provide adequate effectiveness in all desirable circumstances. Quaternary amine compounds likewise possess shortcomings in that they can induce cell toxicity with host cells, which adversely affects the continued viability of fully functioning tissues adjacent to the biomedical implant. While the cytotoxicity of quaternary amine compounds is relatively mild, it is possible to observe in in vitro cell culture experiments that the shape and biological functions of cells in contact with such compounds are substantially affected.

Furanone compounds have been reported to be effective agents against bacterial proliferation and to have antifungal properties (see for example Reichelt and Borowitzka (1984) Hydrobiologia 116: 158-168 and International Patent Application Nos. PCT/AU99/00284 and PCT/AU96/00167, the disclosures of which are incorporated herein by reference). They are thought to act by interfering with bacterial properties that are regulated by acylated homoserine lactones, (AHLs) and two component phosphorelay signal transduction systems. These are fundamental regulatory agents which are widespread in bacteria, including human pathogens (see for example International Patent Application Nos. PCT/AU96/00167 and PCT/AU00/01553, the disclosures of which is incorporated herein by reference).

The AHL regulatory systems in bacteria are one type of signal transduction systems which regulate intercellular activity in response to environmental conditions and extracellular signal molecules. This system was first discovered in the bioluminescent mane bacteria *Vibrio harveyi* and *V. fischeri* where it is used to control expression of bioluminescence. In principle, the system is comprised of two proteins—LuxR and LuxI. The LuxI enzyme is encoded by a luxI gene and produces a related family of signal molecules known as the acylated homoserine lactones (AHLs). These signal molecules bind to the LuxR regulator which is then activated and serves both as a positive regulator for the structural genes which encode the enzymes responsible for bioluminescence, and as a positive regulator for the luxI gene itself. The entire system is amplified via a process of auto induction. Additional molecules serve as regulators of the LuxR-LuxI system.

While initially discovered for bioluminescent bacteria, this regulatory system has now been found in numerous other microorganisms, and is involved in a wide variety of bacterial activities (Pesci and Iglewski, 1999, In Cell-cell signaling in bacteria. Dunny and Winans (eds), ASM Press, Washington D.C., Stevens and Greenberg, 1999 In Cell-cell signaling in bacteria. Dunny and Winans (eds), ASM Press, Washington D.C., Pierson et al. 1998, Annu. Rev. Phytopathol. 36:207-225). These activities include, but are not restricted to exoenzyme production in the plant pathogen *Erwinia carotovora* and exoenzyme and virulence factor production in *Pseudomonas aeruginosa*, the causative agent of cystic fibrosis, and Ti plasmid transfer from *Agrobacterium tumefaciens* to plants. In all instances acylated homoserine lactone, or homoserine lactone-like compounds are the regulatory autoinducers.

Two-component phosphorelay signal transduction systems represent another mechanism, which is distinct from the AHL system described above, by which bacteria sense and respond to their environment (see PCT/AU00/01553). Two-component transduction systems play important roles in the growth and maintenance and functionality of many different microorganisms. Examples include, but are not limited to, regulation of the production of exopolysaccharides and virulence factors; the regulation of motility, swarming, attachment and biofilm formation; and maintenance of viability.

Since these regulatory systems are widespread among bacteria and because they control processes leading to bacterial invasion of host organisms, it is likely that other organisms will have evolved defense mechanisms against these systems.

Natural furanones and their synthetic analogues have been shown to inhibit bacterial adhesion (PCT/AU96/00167). The presumed mode of action of interfering with the regulation of AHL and two component phosphorelay systems entails that the compounds should be capable of diffusing into and through the bacterial cell in order to reach the target site. As a result, soluble, low-molecular weight furanones have been used to date as antibacterial agents.

However, surprisingly, we have found that furanone compounds immobilized onto polymeric substrate surfaces by stable covalent bonds still maintain antibacterial activity, in preventing bacterial proliferation on that substrate material. This surprising finding is at odds with the presumed intracellular action of furanone compounds as AHL mimics, and their ability to interfere with signal transduction through the two-component phosphorelay systems and cannot be explained at present with a well-supported mechanistic model.

DESCRIPTION OF INVENTION

Accordingly, in a first aspect, the present invention provides a substrate having a plurality of immobilised furanone moieties associated with at least part of a surface of the substrate.

By "associated with at least part of a surface of the substrate" is meant immobilization directly onto at least part of the surface of the material of the substrate or via one or more intermediate layers interposed between the substrate material and the immobilised layer. The intermediate layer(s) may be bonding layer(s).

By the term "furanone moiety" is meant a moiety derived from a furanone compound or an analog of the furanone compound or a combination of two or more furanone compounds.

The furanone moiety may be derived from a natural or synthetic furanone compound.

The furanone compound is preferably a compound of formula:

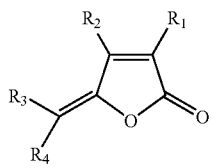

wherein $R_1$ is a moiety selected from the group consisting of H, halogen, formyl, carboxyl, cyano, ester, amide, alkyl, alkoxy, oxoalkyl, alkenyl, alkynyl, aryl or arylalkyl, which moiety may optionally be substituted by one or more substituents; and/or interrupted by one or more hetero atoms; and/or straight chain, branched chain, hydrophobic, hydrophilic or fluorophilic;

$R_2$, $R_3$ and $R_4$ are independently or all H or halogen;

and "═" represents either a double bond or a single bond.

In the formula, a particular geometry is not to be taken as specified. For example, the formula covers both Z- and E-isomers.

Examples of suitable furanone compounds are those disclosed in International Patent Application Nos. PCT/AU95/00407, PCT/AU96/00167, PCT/AU98/00508 and PCT/AU99/00285, the entire disclosures of which are incorporated herein by cross-reference.

The immobilized furanone moieties may be derived from one furanone compound or a plurality of different furanone compounds selected, for example, for both their antibacterial activity and absence of cytotoxicity as well as any other adverse biomedical effect on the host environment that the coated substrate contacts.

The substrate may be shaped or non-shaped. The substrate may be solid, semi-solid or flexible. The substrate may be a woven or non-woven film or sheet. The substrate may be a natural or synthetic filament or fibre. The substrate may be a natural material, for example, a plant seed. The material from which the substrate is formed may be selected to suit the particular application. For example, in the case of a shaped biomedical device the material may meet other specifications of the application, such as mechanical and optical properties.

The invention, in a second aspect, includes an article consisting of or including a substrate in accordance with the first aspect of the invention.

Examples of articles include, but are not limited to, implantable biomedical devices such as urinary catheters, percutaneous access catheters, stents, as well as non-implantable devices such as contact lenses, contact lens storage cases, and the like.

The material from which the article is formed can be a metal, a ceramic, a solid synthetic polymer, or a solid natural polymer, for example a solid biopolymer. Examples of useful materials for this invention are titanium, hydroxyapatite, polyethylene (which are useful materials for orthopaedic implants), polyurethanes, organosiloxane polymers, perfluorinated polymers (which are useful materials for instance for catheters, soft tissue augmentation, and blood contacting devices such as heart valves), acrylic hydrogel polymers and siloxane hydrogel polymers (for instance for contact lens and intraocular lens applications), and the like, and any combination thereof. The surfaces of these materials can be chemically inert or contain reactive functional groups.

In this specification the term "substituted" means that a group may or may not be further substituted with one or more groups selected from alkyl, cycloalkyl, alkenyl, alkynyl, halo, haloalkyl, haloalkynyl, hydroxy, alkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenacyl, alkynylacyl, acylamino, diacylamino, acyloxy, alkylsulfonyloxy, heterocyclyl, heterocycloxy, heterocyclamino, haloheterocyclyl, alkylsulfenyl, carboalkoxy, alkylthio, acylthio, phosphorus-containing groups such as phosphono and phosphinyl.

The term "alkyl", used either alone or in compound words such as "haloalkyl" or "alkylthio", denotes straight chain or branched $C_{1-6}$ alkyl groups. Examples include methyl, ethyl, propyl, isopropyl and the like.

The term "alkoxy" denotes straight chain or branched alkoxy, preferably $C_{1-10}$ alkoxy. Examples include methoxy, ethoxy, n-propoxy, isopropoxy and the different butoxy isomers.

The term "alkenyl" denotes groups formed from straight chain, branched or mono- or polycyclic alkenes including ethylenically mono- or poly-unsaturated alkyl or cycloalkyl groups as previously defined, preferably $C_{2-10}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, or 1,3,5,7-cyclooctatetraenyl.

The term "halogen" denotes fluorine, chlorine, bromine or iodine, preferably bromine or fluorine.

The term "heteroatoms" denotes O, N or S.

The term "acyl" used either alone or in compound words such as "acyloxy", "acylthio", "acylamino" or diacylamino" denotes carbamoyl, aliphatic acyl group and acyl group containing a heterocyclic ring which is referred to as heterocyclic acyl, preferably $C_{1-10}$ acyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkylcarbonyl such as cyclopopylcarbonyl cyclobutylcarbonyl, cyclopentylcarbonyl or cyclohexylcarbonyl; alkylsulfonyl, such as methylsulfonyl or ethylsulfonyl; alkoxysulfonyl, such as methoxysulfonyl or ethoxysulfonyl; heterocyclylcarbonyl; heterocyclylalkanoyl, such as pyrrolidinylacetyl, pyrrolidinylpropanoyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; or heterocyclylglyoxyloyl, such as, thiazolidinylglyoxyloyl or pyrrolidinylglyoxyloyl.

The term "fluorophilic" is used to indicate the highly attractive interactions certain groups, such as highly fluorinated alkyl groups of C4-C10 chain length, have for perfluoroalkanes and perfluoroalkane polymers.

The present invention also has application in any article in non-biomedical areas that requires increased resistance to bacterial colonization. For example, female hygiene products and food preparation and storage ware. In each case the nature and properties of the substrate are selected for that purpose.

As some furanone compounds also possess antifungal properties, the process of surface coating by the process of this invention may also be used to protect materials and devices from fungal attack. Examples include archival documents, antiques and art, rare and valuable seeds intended for storage (e.g. seed banks of conservation groups), etc in which case the substrate may be paper, material or other natural or synthetic material.

In a third aspect, the present invention provides a method of forming an antimicrobial and/or antifungal layer on a substrate including:

(a) providing a substrate;
(b) providing at least one furanone compound or an analog thereof;
(c) optionally treating at least part of the surface of the substrate to activate the surface;
(d) reacting the at least one furanone compound or an analog thereof; with the optionally treated surface to immobilize the at least one furanone or analog.

Reference to at least part of the surface of the substrate includes a surface of one or more intermediate layers applied to the substrate.

The furanone compound(s) may be immobilised on the substrate surface by any suitable technique. Immobilization may be by covalent or non-covalent means. Preferably, the furanone compounds are immobilized on the substrate surface by means of covalent bonds.

Accordingly, in a fourth aspect the present invention provides a substrate according to the first aspect wherein the furanone moieties are covalently bonded to a surface of the substrate.

The immobilization of furanone compounds on to the substrate prevents their loss from the surface, thus ensuring long-lasting antimicrobial action.

The substrates in accordance with the present invention may be characterised by the formula:

X—Y-Z where X is a substrate, Y is an optional chemical King moiety and Z is a furanone moiety. The linking moiety, if present, may be a homobifunctional or heterobifunctional linking moiety. Y may be a simple component (eg a short molecule) or it may comprise a plurality of units or components that may be the same of different Y may comprise a number of components or units that may be "built up" in a stepwise fashion.

The formation of a covalent interfacial linkage is much preferable to an ionic bond since in biological media where the salt content is such that ionic bonds are interfered with and ironically attached molecules can be displaced from a surface.

The covalent anchoring of the furanone compound(s) also serves to eliminate concerns regarding possible deleterious effects that furanone compounds might cause at sites distant from the biomedical device, such as in the liver, brain, or kidney tissues of a living human organism. In medical applications it is important to anchor the furanone compound(s) via an interfacial covalent bond that is not subject to cleavage in the biomedical host environment that the biomedical device is to be placed in.

Methods for the covalent immobilization of organic molecules onto solid surfaces are well known to those skilled in the art Interfacial reactions leading to the formation of covalent interfacial bonds are derived from well-known organic-synthetic reactions. The choice of immobilization reaction depends on both the nature of the substrate material and the chemical composition of the furanone derivative(s) that are desired for a particular application.

For example, a furanone derivative that contains a hydroxyl group in a side chain distal to the furanone ring system, can be linked covalently onto surfaces using epoxide chemistry analogous to the reaction pathway described for the immobilization of polysaccharides onto epoxidated surfaces in Li et al., Surface Modification of Polymeric Biomaterials (B D Ratner and D G Castner, Eds), Plenum Press, NY, 1996 pages 165-173 (the disclosure of which is incorporated herein in its entirety), through isocyanate groups attached to the surface to produce stable urethane linkages through thermal processes, or through carboxylic acid groups or their equivalents, such as acid chlorides, on the surface to produce ester linkages. A furanone derivative that contains an aldehyde group can be linked onto surface amine groups using a reductive amination reaction. A furanone derivative that contains a carboxylic acid group can be linked onto surface amine groups using carbodiimide chemistry. Other immobilization strategies are described in the Examples below.

Interfacial coupling reactions must of course be selected not only for their ability to achieve the desired covalent linkage but also for avoidance of adverse effects on the furanone compound(s) to be attached. Particularly, the furanone ring system tends to be labile to alkaline conditions. Such limitations are well known to those skilled in the art. Among the many possible interfacial coupling reactions known in the art, there is sufficient scope for selection of reactions that proceed in a suitable pH range and with furanones substituted with various functional groups in various positions.

The wide range of interfacial reactions that can be used in the present invention enables the skilled practitioner to select one or more furanone compounds for their particularly high effectiveness against the key bacteria to be combated in a particular biomedical application (as well as absence of adverse effects on the host system), and then design an interfacial linking reaction that can effectively produce a stable coating of such furanone compounds. This is more advantageous than having to select a furanone compound for its compatibility with a particular manufacturing method.

Some solid substrate materials possess reactive surface chemical groups that can undergo chemical reactions with a partner group on a furanone molecule and thereby form a covalent interfacial linkage directly. Alternatively, in situ covalent linkage can be made directly through the addition of a doubly functionalised linker molecule to the active surface in the presence of an appropriate furanone, or stepwise by sequential addition of doubly functionalised linker molecules and then an appropriate furanone. It is not always possible to immobilize furanone compounds directly onto solid substrate materials; in these cases, surface activation or one or more interfacial bonding layer(s) is used to effect covalent immobilization of the furanones. Such surface activation is essential when immobilizing furanone compounds onto polymeric materials such as fluoropolymers and polyolefins.

Surface activation of solid substrate materials can be achieved in a number of ways. Examples are corona discharge treatment or low pressure plasma treatment of polymers.

These methods are well known to introduce a variety of functional groups onto polymeric surfaces.

An alternative approach is to provide an interfacial bonding layer interspersed between the solid substrate material or biomedical device and the furanone layer The application of a thin interfacial bonding layer can be done using methods such as dip coating, spin coating, or plasma polymerization. The chemistry of the bonding layer is selected such that appropriate reactive chemical groups are provided on the surface of this layer, groups that then are accessible for reaction with furanone molecules.

Particularly versatile is the subsequent application of multiple thin interfacial bonding layers; this method can provide a very wide range of desired chemical groups on the surface for the immobilization of a wide range of functionalized furanones and enables usage of furanone compounds optimized for their biological efficacy.

The present invention, in its preferred forms, overcomes the shortcomings of the prior art. It provides surface-immobilized layers comprising one or several chemical compounds from the class of compounds known as furanones or their analogs. One attractive feature of this class of compounds is that a substantial number of them are not cytotoxic to human or other mammalian cells and consequently can be selected to be biocompatible with a particular host environment, so that adverse effects on adjacent host cells are eliminated while antibacterial action is maintained. Moreover, by providing a thin, surface-coated layer of furanone compounds, the optical quality of antibacterial devices of this invention is not reduced, which makes the invention applicable to transparent ophthalmic devices such as contact lenses and intraocular lenses.

The present invention provides thin surface coatings that provide antimicrobial properties and/or antifungal properties to solid materials onto which the coatings have been applied. More particularly, the coatings may be designed to reduce or prevent colonization of biomedical devices by bacteria that cause adverse effects on the health of human users of biomedical devices when such devices are colonized by bacteria.

The active antibacterial layer comprises one or a plurality of furanone compounds selected for both their antibacterial activity and absence of cytotoxicity as well as any other adverse biomedical effect on the host environment that the coated device contacts.

In order that the present invention may be more readily understood, we provide the following non-limiting embodiments.

EMBODIMENTS OF THE INVENTION

COMPARATIVE EXAMPLE 1

(FEP)

Perfluorinated poly(ethylene-co-propylene) polymer (Teflon FEP, DuPont, 100A) in flat sheet form was washed carefully to remove loose surface contamination. Analysis by X-ray photoelectron spectroscopy (XPS) (Kratos AXIS HSi, monochromatic excitation) demonstrated absence of contaminants, which might interfere with bacterial assays. The results of elemental analysis of the surface using XPS are shown in Table 1.

COMPARATIVE EXAMPLE 2

(FEP-HAPP)

A thin coating of a plasma polymer layer having surface amine groups (HAPP) was deposited onto Teflon FEP sheet material from plasma-activated heptylamine vapour as generally described in Griesser and Chatelier, Journal of Applied Polymer Science, Applied Polymer Symposium Vol. 46. Pages 361-384 (1990). Specifically, a piece of FEP sheet material of 12×60 mm is placed in a plasma deposition apparatus as described in the above reference and the apparatus is evacuated to a pressure of $10^{-3}$ mmHg. After establishing a constant flow of vapour evaporating off the monomer liquid n-heptylamine at a chamber pressure of 0.125 mmHg, the plasma deposition is carried out at a power of 20 W and a frequency of 200 kHz. After 20 sec deposition time, the sample is removed from the deposition apparatus and brought in contact with air.

XPS analyses confirmed successful deposition of this layer, by results in accordance with the above publication The results of elemental analysis of the surface using XPS are shown in Table 1. This amine-containing interfacial bonding layer was used for subsequent reactions as described below. The amine-containing bonding layer (FEP-HAPP) was also used as a control in bacterial adhesion and colonization assays described below.

COMPARATIVE EXAMPLE 3

(FEP-HAPP-PAAC)

Onto a sample of FEP coated with a heptylamine plasma polymer layer as per the above example, a further interfacial bonding layer was applied by transferring the amine-coated FEP sample immediately after plasma deposition to a flask containing 30 ml of a 0.1% aqueous solution of poly(acrylic acid), MW 250,000 (Aldrich) at pH 4.0. Immediately after adding the sample, 150 mg of N-(3-dimethylaminopropyl)-N'-ethylcarbodiimide hydrochloride EDC (Sigma) are dissolved in the solution. The sample was left at 4° C. under occasional shaking for 16 h for reaction, following which it was extensively washed with water to remove loosely bound (non-covalently adsorbed) poly(acrylic acid) (PAAC).

After rinsing, the presence of a covalently attached layer of polyacrylic acid was verified by XPS analysis, which showed the expected carboxyl contribution at 289 eV. The results of elemental analysis of the surface using XPS are shown in Table 1.

COMPARATIVE EXAMPLE 4

(FEP-HAPP-PAAC-AZA)

Onto a carboxylated surface prepared as in Comparative Example 3, a layer of 4-azidoaniline was covalently attached by immersing a sample in 30 ml of an aqueous 2 mg/ml solution of 4-azidoaniline hydrochloride (Fluka) buffered to pH 8.8, which was prepared under darkroom conditions. Immediately after adding the poly(acrylic acid)-coated FEP substrate to the solution, 150 mg EDC is added to the solution. After incubating the sample for 16 h at 4° C. in the dark, the sample was taken out of the solution, extensively washed with water and dried. This created an outermost surface possessing azide groups (AZA). The successful application of this azide layer was documented by the expected increase in the nitrogen signal as measured by XPS. The results of elemental analysis of the surface using XPS are shown in Table 1. Samples coated thus were also used as a control in bacterial adhesion and colonisation assays.

EXAMPLE 5

(FEP-HAPP-PAAC-AZA-furanone "24")

Onto an azide surface prepared as in Comparative Example 4, a furanone derivative of the formula

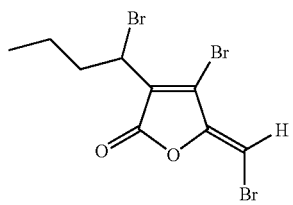

(furanone "24") was immobilized by reaction between the surface azide groups and the furanone compound under the following conditions; Still in the dark, the compound was evenly applied to the modified FEP surface in a 200 mg/ml acetone solution. After complete evaporation of the acetone, the sample was irradiated for 12 min under a UV lamp at 40 W/cm$^2$ and finally extensively washed with ethanol and air dried. The furanone-coated sample thus produced was analyzed by XPS to verify successful coating. The results of elemental analysis of the surface using XPS are shown in Table 1.

It is important to verify that the furanone compounds are indeed covalently bonded to the underlying interfacial bonding layer, as opposed to adsorbed by physical forces, in which case at least a portion of the layer might be leached from the biomedical device and consequently the desired antibacterial function would not be maintained. This was tested by performing the same set of operations but omitting the UV light activation of azide reaction. After applying the furanone compound under these conditions, it could be washed off completely, as attested by a Br signal close to background in XPS on the washed sample.

Samples coated thus (FEP-HAPP-PAAC-AZA-furanone "24") were subjected to bacterial adhesion and colonization assays as described below.

EXAMPLE 6

(FEP-HAPP-PAAC-AZA-furanone "4")

The covalent immobilization of the furanone compound

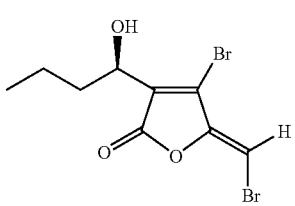

to an FEP polymer substrate was carried out using the same procedures as in Example 5. XPS analysis for Br was used to ascertain successful surface immobilization of the furanone compound. The results of elemental analysis of the surface using XPS are shown in Table 1. Samples coated thus were subjected to bacterial adhesion and colonization assays as described below.

TABLE 1

| Sample | % Si | % F | % C | % O | % N | % Br | Br/C |
|---|---|---|---|---|---|---|---|
| FEP (Comp. Example 1) | 0 | 66.2 | 33.5 | 0 | 0 | 0 | 0 |
| FEP-HAPP (Comp. Ex. 2) | 0 | 0 | 83.3 | 9.1 | 7.6 | 0 | 0 |
| FEP-HAPP-PAAC (Comp. Ex. 3) | 0 | 0 | 71.2 | 22.9 | 5.4 | 0 | 0 |
| FEP-HAPP-PAAC-AZA (Comp. Ex. 4) | 0 | 0 | 72.9 | 11.5 | 15.6 | 0 | 0 |
| FEP-HAPP-PAAC-AZA-furanone "4" (Example 6) | 0 | 0.1 | 75.4 | 14.4 | 7.94 | 1.16 | 0.015 |
| FEP-EAPP-PAAC-AZA-furanone "24" Example 5 | | 0.21 | 75.1 | 12.64 | 10.74 | 1.31 | 0.017 |

EXAMPLE 7

(FEP-HAPP-PAAC-AZA-furanone "22")

The covalent immobilization of the compound (furanone "22")

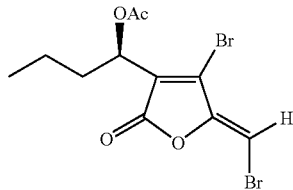

to an FEP polymer substrate was carried out using the same procedures as in Example 5. Samples coated thus were subjected to bacterial adhesion and colonization assays as described below.

EXAMPLE 8

(FEP-HAPP-HMDI-furanone "4")

The covalent immobilization of the furanone compound (furanone "4")

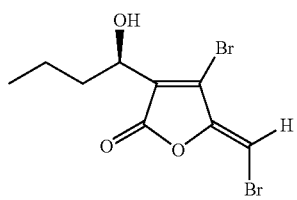

to an FEP polymer substrate was carried out as follows: a sample of FEP sheeting of 12×20 mm was placed in a plasma deposition apparatus and coated with a plasma polymer layer from the process vapour n-heptylamine at a pressure of 0.125 mmHg, at a power of 20 W, and a frequency of 200 kHz. After 20 s deposition time, the sample was removed from the plasma deposition apparatus and transferred to a container holding 10 ml of a 10% (v/v) solution of hexamethylene diisocyanate HMDI (Aldrich) in acetonitrile. After incubation for 24 h at room temperature, the sample was washed extensively with acetonitrile and transferred into 10 ml of a acetonitrile solution containing 0.2 ml of the furanone compound. After incubation for 72 h at room temperature, the sample was removed from the solution, washed extensively with acetonitrile, and finally air dried. XPS analysis for Br was used to ascertain successful surface immobilization of the furanone compound. The results of elemental analysis of the surface using XPS are shown in Table 2. The samples thus coated were subjected to bacterial adhesion and colonization assays as described below.

TABLE 2

| Sample | % Si | % F | % C | % O | % N | % Br | Br/C |
|---|---|---|---|---|---|---|---|
| FEP | 0 | 66.2 | 33.5 | 0 | 0 | 0 | 0 |
| FEP-HAPP | 0 | 0 | 83.3 | 9.1 | 76 | 0 | 0 |
| FEP-HAPP-HMDI | 0.67 | 0 | 76.55 | 15.36 | 7.41 | 0 | 0 |
| FEP-HAPP-HMDI-furanone "4" covalent | 0 | 0 | 75.26 | 14.09 | 5.7 | 4.86 | 0.065 |

Bacterial Adhesion and Colonization Assays

The bacterium used in the assays was *Pseudomonas aeruginosa* strain 6294. Bacterial cells were grown overnight at 35° C. in trypticase soy broth, harvested by centrifugation (3,000 g), washed three times in phosphate buffered (pH 7.0) saline (PBS) and finally resuspended in PBS to an optical density at 660 nm of 0.1. Bacterial cells (0.5 ml) were then added to the materials (with covalently attached furanones or without furanones as controls), and allowed to adhere at 35° C. for 10 min. After 10 min non-adhered or loosely adhered cells were removed by washing in PBS (3×1 ml). Materials were then either analyzed for total number of bacterial cells adherent (initial adhesion), or alternatively, materials were transferred into 0.5 ml of fresh TSB and incubated for 5 h at 35° C. incubator. After the incubation, the materials were analyzed for total numbers of bacterial cells (biofilm).

Materials used in the tests were: FEP-HAPP (control surface for HAPP-HMDI-coating), FEP-HAPP-HMDI-furanone "4", FEP-HAPP-PAAC-AZA-furanone "4", FEP-HAPP-PAAC-AZA (control surface for azide coating), FEP-HAPP-PAAC-AZA-furanone "24", FEP-HAPP-PAAC-AZA-furanone "22".

Bacterial adhesion was measured by staining the materials with crystal violet. After rinsing off the stain, the number of bacteria adherent to the surface was estimated by microscopic count. Results are presented (Table 3) as percentage reduction compared to adhesion to control (FEP-HAPP) in the initial adhesion and biofilm assays.

TABLE 3

| | Initial adhesion | Biofilm formation |
|---|---|---|
| FEP-HAPP-HMDI furanone "4" | 68% | −16% |
| FEP-HAPP-PAAC-AZA-furanone "4" | 47% | 53% |
| FEP-HAPP-PAAC-AZA-furanone "24" | 42% | 62% |
| FEP-HAPP-PAAC-AZA-furanone "22" | 35% | 40% |

Negative values indicate increase in adhesion/biofilm formation compared to control.

EXAMPLE 9

Attachment of Furanones to Cotton and Woollen Surfaces

The attachment method is based on a chemical (cyanuric chloride) which is used extensively in the dyestuffs industry for attachment of one or two separate dyes to a fibre surface. This molecule has three active sites, one or two of which can be replaced by the dyestuff and the remaining becomes a focus of attack by hydroxyl or amino-groups present in the fibre (e.g. cotton fibres or wool fibres).

A similar strategy as outlined below may be used for attaching furanones to cotton and woollen surfaces. This involves reacting cyanuric chloride with one or two molecules of appropriate furanone followed by reaction with cotton or woollen fibres, which have free hydroxyl and amino groups respectively on their surface.

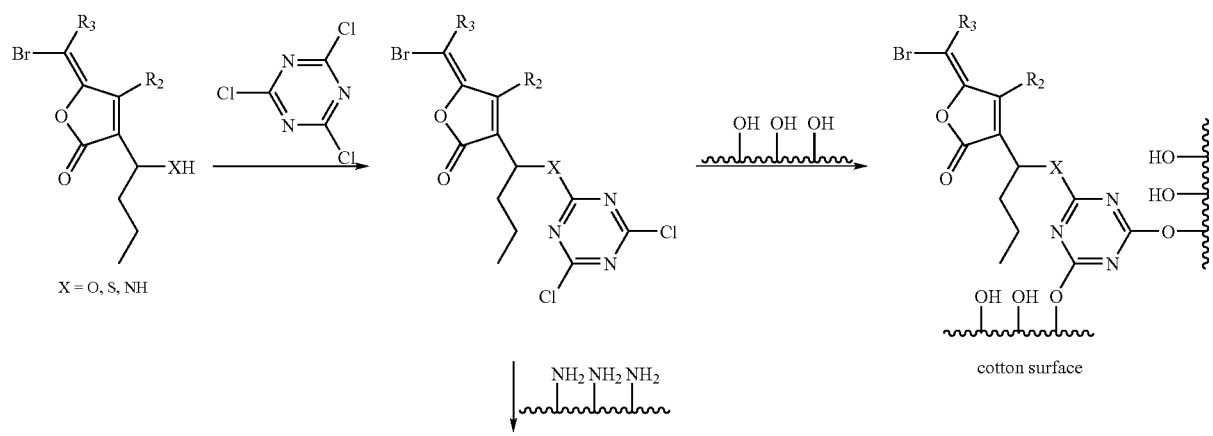

-continued

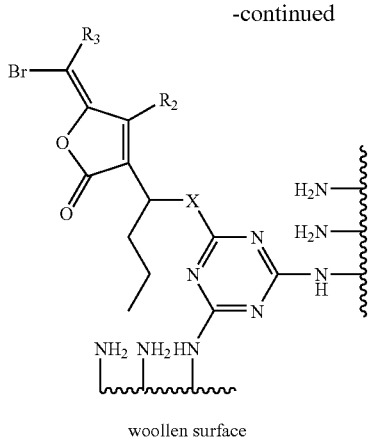

woollen surface

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A substrate having a plurality of immobilized furanone moieties associated with at least part of a surface of the substrate, wherein the furanone moieties are derived from at least one compound selected from the group consisting of a furanone compound and an analog thereof wherein the furanone moieties are covalently bonded to functional groups on the surface of the substrate; and wherein the furanone compound is of the formula

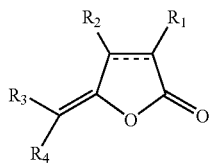

wherein $R_1$ is a moiety selected from the group consisting of H, halogen, formyl, carboxyl, cyano, ester, amide, alkyl, alkoxy, oxosikyl, alkenyl, alkynyl, aryl and arylalkyl, which moiety may optionally be
substituted by one more substituents; and/or
interrupted by one or more hetero atoms; and/or
straight chain, branched chain, hydrophobic, hydrophilic and/or fluorophilic;
$R_2$, $R_3$ and $R_4$ are independently or all H or halogen; and

- - - - - represents either a double bond or a single bond.

2. A substrate according to claim 1, wherein furanone moieties are derived from at least two different furanone compounds, at least two different furanone analogs or a combination of said furanone compounds and analogs.

3. A substrate according to claim 1, wherein the furanone compound is a naturally occurring furanone.

4. A substrate according to claim 1, wherein the furanone compound is a synthetic furanone.

5. A substrate according to claim 1, wherein the substrate comprises a material selected from at least one of the group consisting of metals, ceramics, glasses, natural polymers, synthetic polymers and natural materials.

6. A substrate according to claim 5, wherein the material is selected from the group consisting of noble metals, titanium, steel, hydroxyapatite, ethylene polymers and copolymers, polyurethanes, organosiloxanes perfluorinated polymers, acrylic hydrogel polymers and copolyrners, siloxane hydrogel polymers and copolymers and natural and synthetic elastomers.

7. A substrate according to claim 5, wherein the natural material is selected from the group consisting of seeds, grains, seed products, fibres wool, hair, silk, cotton, chitin, collagen, animal organs and animal hides.

8. A substrate according to claim 1, wherein the substrate is solid, semi-solid, rigid or flexible.

9. A substrate according to claim 1, which is shaped.

10. A substrate according to claim 1, in the form of a natural or synthetic filament or fibre.

11. A substrate according to claim 10, wherein the fibre is a natural fibre selected from wool, cotton and hemp.

12. A substrate according to claim 1, in the form of a woven or non-woven film, sheet or textile.

13. A substrate according claim 1, which is formed from a material that is suitable for use in a biomedical application.

14. A method of forming an antimicrobial and/or antifungal layer on a substrate including:
    (a) providing a substrate,
    (b) providing at least one furanone compound or an analog thereof;
    (c) treating at least part of the surface of the substrate to introduce functional groups to the surface; and;
    (d) reacting the at least one furanone compound or an analog thereof with the functional groups on the treated surface to immobilize the at least one furanone or analog thereof wherein the immobilization on the surface is by means of covalent bonding;
wherein step (c) is selected from the group consisting of corona discharge treatment;
low pressure plasma treatment;

introducing reactive aryl azide intermediates to the surface followed by exposure to UV light; and
radiofrequency plasma discharge in the presence of water; and wherein the furanone compound is of the formula:

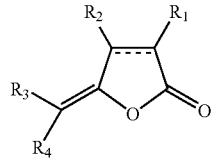

wherein $R_1$ is a moiety selected from the group consisting of H, halogen, formyl carboxyl, cyano, ester, amide, alkyl, alkoxy, oxoalkyl, alkenyl, alkynyl, aryl or arylalky which moiety may optionally be
substituted by one or more substituents; and/or
interrupted by one or more hetero atoms; and/or
straight chain, branched chain, hydrophobic, hydrophilic and/or fluorophilic;

$R_2$, $R_3$ and $R_4$ are independently or all H or halogen; and

----- represents either a double bond or a single bond.

15. A substrate according to claim 1, wherein the surface of the substrate has been subjected to surface activation to introduce said functional groups onto the surface prior to immobilization of the furanone moieties.

16. A substrate according to claim 15, wherein the surface activation is selected from the group consisting of:
   (i) corona discharge treatment;
   (ii) low pressure plasma treatment;
   (iii) introducing reactive aryl azide intermediates to the surface followed by exposure to UV light; and
   (iv) radiofrequency plasma discharge in the presence of water.

* * * * *